United States Patent [19]

Jackson et al.

[11] Patent Number: 5,578,641
[45] Date of Patent: Nov. 26, 1996

[54] COSMETIC COMPOSITION

[75] Inventors: Simon M. Jackson, West Los Angeles, Calif.; Anthony V. Rawlings, Wyckoff; Ian R. Scott, Allendale, both of N.J.

[73] Assignee: Elizabeth Arden Co., Division of Conopco, Inc., New York, N.Y.

[21] Appl. No.: 230,366

[22] Filed: Apr. 20, 1994

[30] Foreign Application Priority Data

Apr. 20, 1993 [GB] United Kingdom .................. 9308103

[51] Int. Cl.$^6$ ...................................................... A61K 7/48
[52] U.S. Cl. .......................... 514/547; 424/401; 514/844; 514/847
[58] Field of Search ............................ 424/401; 514/844, 514/847, 547

[56] References Cited

U.S. PATENT DOCUMENTS

| | | | |
|---|---|---|---|
| 4,294,852 | 10/1981 | Wildnauer | 424/317 |
| 4,595,591 | 6/1986 | Mardi | 424/127 |
| 4,885,157 | 12/1989 | Fiaschetti | 424/59 |
| 5,326,565 | 7/1994 | Critchley | 424/401 |
| 5,342,976 | 8/1994 | Bowser | 554/36 |

FOREIGN PATENT DOCUMENTS

| | | |
|---|---|---|
| 669090 | 3/1966 | Belgium . |
| 0107885 | 5/1984 | European Pat. Off. . |
| 2654618 | 5/1991 | France . |
| 2692781 | 12/1993 | France . |
| 61-0251607 | 11/1986 | Japan . |
| 30123733 | 5/1991 | Japan . |
| 40005219 | 1/1992 | Japan . |
| 5085924 | 4/1993 | Japan . |
| 88/06034 | 8/1988 | WIPO . |

*Primary Examiner*—C. Warren Ivy
*Assistant Examiner*—Evelyn Huang
*Attorney, Agent, or Firm*—Rimma Mitelman

[57] ABSTRACT

A composition for topical application to skin which comprises:

(i) from 0.0001 to 10% by weight of one or more ceramide pathway intermediates or precursors thereof and mixtures thereof; and (ii) a balancing amount of a cosmetically acceptable vehicle for the intermediate.

9 Claims, 3 Drawing Sheets

CERAMIDE PATHWAYS

COSMETIC COMPOSITION

FIELD OF THE INVENTION

The invention relates to skin-conditioning compositions and methods. It is particularly concerned with the stimulation of ceramide production in the epidermis, leading to an increase in the level of these lipid materials in the stratum corneum of the skin. The composition is also suitable for topical application to the hair and the nails.

BACKGROUND TO THE INVENTION

The stratum corneum, which is the outermost layer of the mammalian skin, contains intercellular lipids consisting predominantly of ceramides, cholesterol and fatty acids. From studies involving lipid depletion of the corneum by solvent extraction and from enzyme inhibition studies, ceramide in particular has been shown to be essential for the barrier function of the stratum corneum.

In normal skin, if there is perturbation of the barrier function, the epidermis normally re-synthesises the deficient lipids by inducing the expression or activation of the appropriate enzymes. However, under certain conditions, a reduced capacity for re-synthesis of the lipids may occur. This is especially so with elderly subjects, whose stratum corneum ceramide level is in any case reportedly lower than that of younger subjects.

The present invention is based upon the concept of stimulating the synthesis of ceramides in the epidermis by the topical application of precursors thereof in the biosynthetic pathway and/or by stimulation of the activity of enzymes responsible for catalysing the steps in the biosynthetic pathway that yields ceramide (as described later in this specification).

Synthesis of Ceramide

The synthesis of ceramide in the epidermis can be achieved by a variety of biochemical pathways, for example, those shown in FIG. 1.

Common to each of these pathways are palmitoyl-CoA and serine, which are converted initially to 3-ketosphinganine in the presence of serine palmitoyl transferase. This is a rate limiting step and can accordingly adversely affect the rate of synthesis of ceramides via 3-ketosphinganine and the other intermediates as shown in these pathways.

We have now discovered that the rate of synthesis of ceramide in the epidermis can be increased following topical application of one or more intermediates in these biosynthetic pathways, especially those that are distal to the rate limiting step. We have also discovered that precursors comprising palmitoyl CoA and serine, can together increase ceramide synthesis, even though these are proximal to the rate limiting step.

The invention is accordingly concerned with the use of one or more of these ceramide pathway intermediates, following topical application, in enhancing the quality and condition of human skin, especially the water barrier properties thereof, in particular by increasing the rate of ceramide biosynthesis in the epidermis.

DEFINITION OF THE INVENTION

According to the invention, there is provided a composition suitable for topical application to human skin which comprises:

(i) from 0.0001 to 10% by weight of a ceramide pathway intermediate or a precursor thereof or mixtures thereof; and (ii) a balancing amount of a cosmetically acceptable vehicle for the ceramide pathway intermediate or precursor thereof.

The invention is also concerned with a method of treating skin, particularly dry and aged skin, with topically applied ceramide pathway intermediate, or a precursor thereof or mixtures thereof, in order to maintain or repair the skin barrier which controls moisture loss from the skin.

The invention is also concerned with the use of one or more ceramide pathway intermediates, or precursors thereof or mixtures thereof in maintaining or enhancing the skin barrier function which controls moisture loss from the skin and in the treatment of skin to reduce or delay the development of wrinkles associated with advancing age, or with sun-induced skin ageing.

The invention is also concerned with the use of at least 0.0001% by weight based on the total composition, of a ceramide pathway intermediate in a composition suitable for topical application to human skin comprising a major proportion of a cosmetically acceptable vehicle for the ceramide pathway intermediate.

DISCLOSURE OF THE COMPOSITION OF THE INVENTION

The composition according to the invention comprises in its simplest form a ceramide pathway intermediate or a precursor thereof, or mixtures thereof together with a cosmetically acceptable vehicle, the composition being suited for topical application to human skin.

The primary function of the said intermediate or precursor thereof is to stimulate the synthesis of ceramide in the epidermis which then leads to higher ceramide levels in the stratum corneum. The water permeability barrier function of the skin, is thereby improved and the ability of the skin to retain moisture consequently enhanced.

The consumer perceived benefits that accordingly accrue from higher levels of ceramide in the stratum corneum achieved in this way are to be seen in the improvement in skin condition, such as eradication or reversal of skin ageing, including removal of age spots, keratoses, wrinkles, skin lines, blotches, blemishes, nodules, pigmented spots, coarse, rough and dry skin, together with improvements in skin barrier function leading to fewer problems of skin sensitivity, photodamaged skin, loss of elasticity and flexibility.

The Ceramide Pathways

Figure 1:
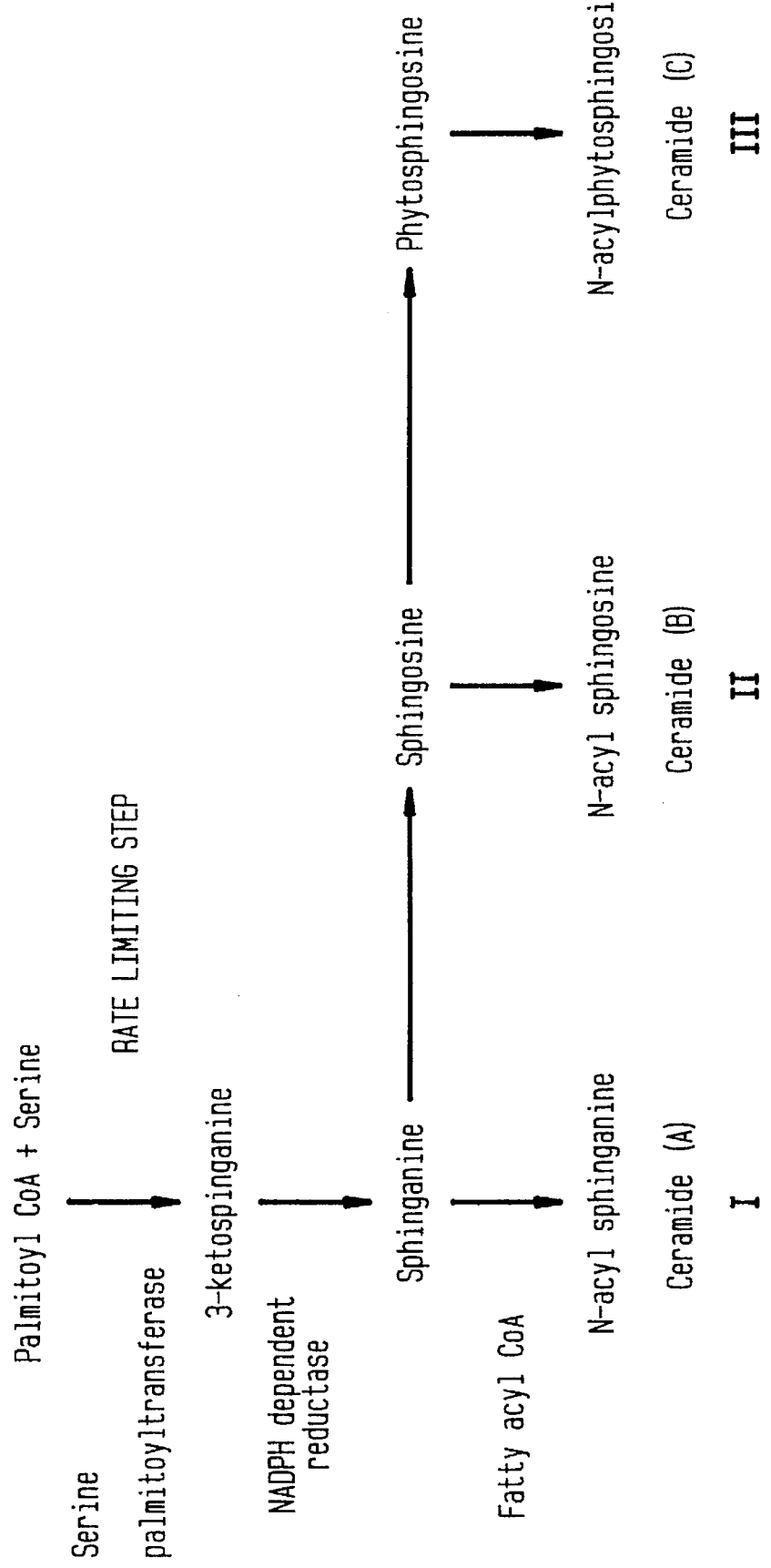
FIG. 1 illustrates the synthesis of ceramide in the epidermis by a variety of biochemical pathways.

With reference to FIG. 1, which shows three alternative biosynthetic pathways for the production of ceramides in human skin, it can be seen that each has a common rate limiting step, namely the conversion of palmitoyl-CoA and serine to 3-ketosphinganine in the presence of serine palmitoyltransferase.

With reference to Ceramide Pathway I (FIG. 1), 3-ketosphinganine is then converted to sphinganine in the presence of NADPH-dependant reductase and final conversion to Ceramide(A), via sphinganine in the presence of fatty acyl-CoA.

With reference to Ceramide Pathway II, 3-ketosphingosine is converted firstly to sphinganine and then secondly to sphingosine, and then to N-acyl sphingosine (Ceramide (B)).

With reference to Ceramide Pathway III, 3-ketosphinganine is converted to sphinganine in the presence of NADPH-dependant reductase, as occurs in Ceramide Pathway I, but then sphinganine is converted firstly to sphingosine, and secondly to phytosphingosine and then to N-acylphytosphingosine (Ceramide (C)).

The Ceramides produced via ceramide pathways I, II and III are likely to be structurally different from each other and for this purpose are designated Ceramides (A), (B) and (C).

It is to be understood that the above ceramide pathways are purely illustrative and do not represent the only pathways available for the production of ceramide.

The Ceramide Pathway Intermediates

As has been explained, the conversion of palmitoyl-CoA and serine to 3-ketosphinganine in the presence of serine palmitoyltransferase represents the rate limiting step, ie the step which limits the formation of ceramide in the skin and other tissues. Accordingly, in order to enhance the rate at which ceramide is formed, particularly in the skin, it is preferred to deliver to the skin an effective amount of a precursor of ceramide which enters one or more of the Ceramide Pathways distal to this rate limiting step.

The rate of formation of ceramide can thus be enhanced by providing as precursors sphingoid bases, typical examples of which are sphinganine, sphingosine and phytosphingosine and derivatives thereof in accordance with structure (1):

$$\begin{array}{c} R^1 \\ NH \\ \phantom{R^1} \diagdown \phantom{OR^2} OR^2 \\ X \diagup OR^3 \end{array} \quad (1)$$

where X is represented by $$R^4 \diagdown = \diagup$$

$$R^4 \diagdown \diagup$$

$$R^4 \diagdown \diagup_{OR^5}$$

or $$R^4 \diagdown = \diagup_{OR^5}$$

and where $R^1$, $R^2$, $R^3$ and $R^5$ are each individually represented by H-, $CH_3(CH_2)_n$-

$$CH_3(CH_2)_n(CHOH)_n-, \quad CH_3(CH_2)_n(CHOH)_n\overset{O}{\underset{\|}{C}}- \quad \text{or}$$

$$CH_3(CH_2)_n\overset{O}{\underset{\|}{C}}-,$$

or phosphorylated, sulphated, glycosylated and benzoyl derivatives thereof;

where n is 0, or an integer of from 1 to 10, and
$R^4$ is $CH_3(CH_2)_m$-
where m is an integer of from 1 to 21.

One preferred group of ceramide pathway intermediates includes: sphinganine, sphingosine and phytosphingosine and their respective N-acyl, O-acyl and N-alkyl derivatives.

A particularly preferred ceramide pathway intermediate is tetraacetyl phytosphingosine having the structure (2):

$$\begin{array}{c} \text{(2)} \\ H_3CC(O)-NH \diagdown \diagup O-CCH_3(O) \\ \phantom{xxx} \diagup \phantom{xx} O-CCH_3(O) \\ H_{27}C_{13} \diagdown \diagup \\ O-CCH_3(O) \end{array}$$

Particularly preferred derivatives of sphinganine are N-acetyl sphinganine having the structure (3):

$$\begin{array}{c} \text{(3)} \\ H_3C-\overset{O}{\underset{\|}{C}}-NH \diagdown \diagup OH \\ H_{27}C_{13} \diagdown \diagup OH \end{array}$$

N-methyl sphinganine having the structure (4):

$$\begin{array}{c} \text{(4)} \\ H_3C-NH \diagdown \diagup OH \\ H_{27}C_{13} \diagdown \diagup OH \end{array}$$

The acyl substituent is suitably a $C_{1-16}$ acyl group preferably acetoxy. Conveniently, the pathway intermediate may be acylated at the N-atom and one or more of the oxygen atom present. The alkyl substituent is suitably $C_{1-16}$, preferably $C_{1-4}$, especially methyl. The nitrogen atom may be mono- or di-alkylated.

N,N¹-dimethylsphinganine having the structure (5):

$$\begin{array}{c} \text{(5)} \\ H_3C \diagdown N \diagup CH_3 \\ \phantom{xxx} \diagdown \diagup OH \\ H_{27}C_{13} \diagdown \diagup OH \end{array}$$

Particular preferred derivatives of sphingosine are -acetylsphingosine having the structure (6):

$$\begin{array}{c} \text{(6)} \\ H_3CC(O)-NH \diagdown \diagup OH \\ H_{27}C_{13} \diagdown = \diagup OH \end{array}$$

N-methyl sphingosine having the structure (7):

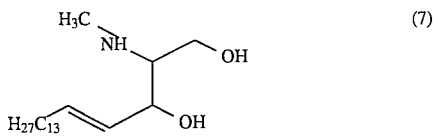

N,N¹-dimethylsphingosine having the structure (8):

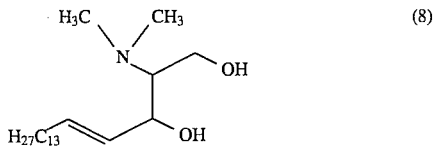

Other particularly preferred derivatives of phytosphingosine are:

N-acetylphytosphingosine having the structure (9):

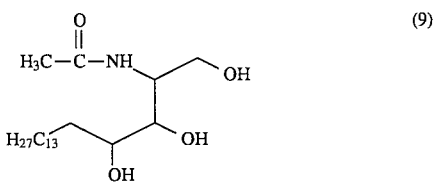

N-methyl phytosphingosine having the structure (10):

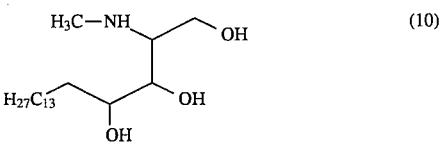

and N,N¹ dimethyl phytosphingosine having the structure (11):

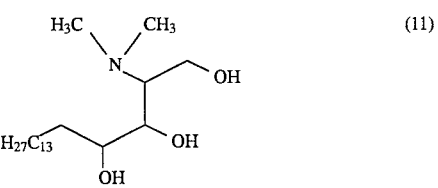

It is to be understood that the above structures (2) to (11) are illustrative of derivatives of ceramide pathway intermediates which are useful in accordance with the invention and that there are many other derivatives that fit structure (1) that are also useful.

As has been explained earlier, it is also possible to employ precursors of ceramide synthesis that occur proximal to the rate limiting step in the ceramide pathway. These precursors are preferably palmitoyl CoA and serine which together are converted to 3-ketosphinganane by the enzyme serine palmitoyltransferase.

The amount of a selected ceramide pathway intermediate including precursors thereof or mixture thereof that should be incorporated in the composition according to the invention is from 0.0001 to 10%, preferably from 0.1 to 5% and ideally from 0.05 to 2% by weight of the composition.

THE COSMETICALLY ACCEPTABLE VEHICLE

The composition according to the invention also comprises a solid, semi-solid or liquid cosmetically and/or physiologically acceptable vehicle, to enable the ceramide pathway intermediate to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the ceramide pathway intermediate which therefore ensure that they can be applied to and distributed evenly over the skin, hair or nails at an appropriate concentration. The vehicle is preferably one which can aid penetration of the ceramide pathway intermediate into the skin to enable it more readily to influence the skin condition.

Compositions according to the invention can include water as a vehicle, and/or at least one cosmetically acceptable vehicle other than water.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, squalane, squalene, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate, ethylene glycol distearate;

The cosmetically acceptable vehicle will usually form from 10 to 99.999%, preferably from 10 to 99% and most preferably from 50 to 99% by weight of the composition, and can, in the absence of other cosmetic adjuncts, form the balance of the composition.

Ceramide Pathway Adjuncts

In the biosynthesis of ceramide as hereinbefore described, the provision of ceramide pathway adjuncts in the composition according to the invention is preferable.

For example, the ceramide pathway intermediates and precursors thereof are preferably accompanied by saturated or unsaturated, straight or branched chain fatty acids or their esters, particularly their coenzyme A derivatives, or adenosine monophosphate derivatives, or preferably alpha-, beta or omega hydroxylated straight or branched chain fatty acids and esters thereof, especially the omega hydroxy linoleoyl ester.

The amount of selected ceramide pathway adjuncts, when employed, can be similar to that of the ceramide pathway intermediate or precursor thereof.

OPTIONAL SKIN BENEFIT MATERIALS AND COSMETIC ADJUNCTS

Penetration Enhancer

The composition according to the invention can also optionally comprise a penetration enhancer which can potentiate the benefit of the ceramide pathway intermediate or precursor thereof by improving its delivery through the stratum corneum to its site of action in the epidermis.

The penetration enhancer can accordingly function in a variety of ways. It can for example, improve the distribution of the ceramide pathway intermediate on the skin surface or, it can increase its partition into the skin from the composition when applied topically, so aiding its passage to its site of action. Other mechanisms enhancing the benefit of the ceramide pathway intermediate may also be involved.

Examples of penetration enhancers include:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane
Tetrahydrofuran
Butan-1,4-diol
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Dibenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate
Butyl stearate
Benzyl salicylate
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one The amount of penetration enhancer, when employed in accordance with the invention, will normally be from 0.1 to 50%, preferably from 0.5 to 25% and most preferably from 0.5 to 10% by weight of the composition.

A particularly convenient form of the composition according to the invention is an emulsion, in which case an oil or oily material will normally be present, together with an emulsifier to provide either a water-in-oil emulsion or an oil-in-water emulsion, depending largely on the average hydrophillic-lyophilic balance (HLB) of the emulsifier employed.

Oil or Oily Material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value.

TABLE I

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Span 60 | 4.7 |
| Polyoxyethylene (2) stearyl ether | Brij 72 | 4.9 |
| Polyoxyethylene sorbital beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monoooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween 60 | 14.9 |
| Polyoxyethylene 20 sorbitan monooleate | Tween 80 | 15.0 |
| Polyoxyethylene (20) stearate | Myrj 49 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight from 10,000 to 50,000.

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Retinoids

The composition according to the invention optionally can also comprise a retinoid, such as retinoic acid or retinol (Vitamin A) and/or derivative thereof, further to enhance the benefits to skin of the ceramide pathway intermediate.

In addition to retinol itself, examples of derivatives of retinol include:
Retinyl acetate
Retinyl butyrate
Retinyl propionate
Retinyl octanoate
Retinyl laurate Retinyl palmitate
Retinyl oleate
Retinyl linoleate, and
Retinyl linolenate.

The amount of retinoid, when present in the composition according to the invention is from 0.01 to 10% and preferably 0.1 to 5% by weight of the composition.

Tocopherol

The composition according to the invention optionally can also comprise a tocopherol (vitamin E group), as an antioxidant for the retinoid, when present in the composition, and to limit oxidative damage to skin. The vitamin E group comprises α-tocopherol, β-tocopherol, γ-tocopherol and δ-tocopherol.

The amount of a tocopherol, when present in the composition according to the invention, is from 0.0001 to 20%, preferably from 0.0001 to 10% by weight of the composition.

Water

The composition of the invention can also comprise water, usually up to 90%, preferably from 5 to 80% by volume. Water can function as the cosmetically acceptable vehicle.

OTHER COSMETIC ADJUNCTS

Examples of other cosmetic adjuncts which can optionally be employed in the composition according to the invention include preservatives, such as para-hydroxy benzoate esters; antioxidants, such as butyl hydroxy toluene; humectants, such as glycerol, sorbitol, 2-pyrrolidone-5-carboxylate, dibutylphthalate, gelatin, polyethylene, glycol, preferably PEG 200–600; buffers, such as lactic acid together with a base such as triethanolamine or sodium hydroxide; surfactants, such as glycerol ethers; ceramides of synthetic, animal or plant origin; pseudoceramides; phospholipids; vitamins, such as 1,25 dihydroxy cholecalciferol; waxes, such as beeswax, ozokerite wax, paraffin wax, plant extracts, such as Aloe vera, cornflower, witch hazel, elderflower, cucumber, thickeners; activity enhancers; colourants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

In a further preferred composition, the ceramide pathway intermediate is combined with ceramides, pseudoceramides, polyol fatty acid polyesters, sterols, particularly cholesterol, galactosyldiacyl-glycerols, glycosphingolipids, fatty acids and esters thereof and mixtures thereof and other ingredients, such as mevalonic acid, hexadecylsuccinic acid monobehenyl ester ethoxylate (7.3 EO) and/or derivatives thereof to produce a liposomal dispersion. Preferred ceramide pathway adjuncts include ceramides, cholesterol, cholesterol pathways intermediates or precursors thereof such as mevalonic acid and fatty acid pathway intermediates or precursors thereof such as acetic acid and malonic acid.

A further preferred composition may also contain in combination with the ceramide pathway intermediate and optional additional ingredients disclosed above, an organic acid component chosen from hydroxy carboxylic acids, such as alpha, beta and omega hydroxyacids, especially glycolic acid, lactic acid and 2-hydroxyoctanoic acid, and keto carboxylic acids, esters thereof and mixtures thereof. It will be appreciated that the invention includes within its scope all enantiomers, diasteromers and mixtures thereof.

In yet another preferred composition, the ceramide pathway intermediate is dissolved in squalene or squalane, optionally together with ceramides and other ingredients, such as mevalonic acid and malonic acid and/or derivatives thereof and formulated with volatile and non-volatile silicones to produce an anhydrous or nearly anhydrous single phase system.

Cosmetic adjuncts can form the balance of the composition.

PRESERVATION OF THE COMPOSITION

The composition according to the invention is preferably preserved in such a manner that it will enjoy an extended shelf life following manufacture and prior to sale and use. Ideally the composition will have an indefinite shelf life.

It is accordingly apparent that the ceramide pathway intermediate is likely to be prone to attack by bacteria, moulds and fungi and other microbial influences, particularly at pH values near that of the skin that characterise the preferred composition. The shelf-life of the composition can therefore be unacceptably short due to the biodegradation of the precursor unless steps are taken to preserve the composition.

In order to be preserved, the composition should preferably be free, or substantially free, from viable microbial contaminants that are capable of resulting in microbial spoilage of the composition, and/or biodegradation of the precursor prior to topical application of the composition to mammalian skin or hair. It is to be understood, however, that the invention is also concerned with compositions, as herein defined, which may contain viable but dormant microorganisms, such as bacterial spores, provided that the conditions of preservation do not result in substantial proliferation of the microorganisms prior to use of the composition.

Examples of the methods that can be employed to achieve preservation of the composition, includes the following:
(i) Sterilisation The composition according to the invention can be preserved by sterilisation to remove or kill substantially all viable microbial contaminants. This can be achieved for example by irradiation using a lethal dose of gamma rays, by heat sterilisation or by ultrafiltration using techniques that are well established in the pharmaceutical industry.
(ii) Chemical Preservative The composition according to the invention can also be preserved by including in it a chemical preservative which functions to prevent the growth of or kill bacteria, fungi or other microorganisms.

Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 5%, preferably from 0.1 to 2% by weight, the amount chosen being sufficient to arrest microbial proliferation.
(iii) Water activity depressants The composition according to the invention can also be preserved by the inclusion of a water activity depressant such as glycerol, propylene glycol, sorbitol, sugars and salts, for examples alkali metal halides gulphates and carboxylates. When employing a water activity depressant, sufficient should be incorporated in the composition according to the invention to reduce the water activity ($\alpha_w$) from 1 to <0.9, preferably to <0.85 and most preferably <0.8, the lowest of these values being that at which yeasts, moulds and fungi will not proliferate.

PROCESS

The invention also provides a process for preparing a composition according to the invention which comprises the steps of mixing an effective amount of a ceramide pathway intermediate, as herein defined, together with a cosmetically acceptable carrier for the intermediate.

USE OF THE COMPOSITION

The composition according to the invention is intended primarily as a product for topical application to human skin, for maintaining or enhancing the skin barrier function, particularly by stimulating the synthesis of ceramides. The composition is particularly useful for treating dry, ageing or damaged skin to reduce moisture loss, increase stratum corneum flexibility and to enhance the quality of skin. The composition can also be applied to the hair or nails.

In use, a small quantity of the composition, for example from 1 to 5 ml, is applied to exposed areas of the skin, hair or nails, from a suitable container or applicator and, if necessary, it is then spread over and/or rubbed into the area to be treated using the hand or fingers or a suitable device.

PRODUCT FORM AND PACKAGING

The topical skin and/or hair and/or nail treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer.

For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

EVIDENCE OF EPIDERMAL LIPID (CERAMIDE) BIOSYNTHESIS

The biosynthesis of epidermal lipid, especially ceramides, can be determined by the method described below.

Results of ceramide biosynthesis from sphingosine as the ceramide pathway intermediate are also given.

In-Vitro Measurement of Epidermal Lipid Biosynthesis

The stimulatory effect of ceramide pathway intermediates (CPI) on lipid levels in the epidermis can be quantified by in-vitro measurements of the level of incorporation of radio-labelled lipid precursors into epidermal lipids over relatively short periods of time (24 hours).

1. Method

Punch biopsies (6 mm) were taken of full thickness skin scraped free of subcutaneous fat, and floated dermis side downwards onto 3 ml of culture medium (MCDB 153 without animal sera, growth factors, or hormones ex Sigma Chemical Co.), containing radiolabelled lipid precursor (4 μCi/ml of 1–14C acetic acid, sodium salt, 7.4 MBq/ml ex Amersham) and CPI (in 96% v/v ethanol vehicle). Following a 24 hour incubation at 37 C. in air (Harvard/LTE incubator), epidermis was isolated from the dermis by incubation in 10 mM ethylenediaminetetraacetic acid solution at 37 C. for 30 minutes, and placed into 3 ml of chloroform:methanol (2:1 v/v) solution for lipid extraction. After 18 hours 0.75 ml of potassium chloride solution (0.88% w/v) was added with mixing which after centrifugation produced 2 liquid phases, an upper aqueous phase, and a lower organic phase containing the lipids. Beckman ReadySafe scintillation fluid (4 ml) was added to 100 μl aliquots of the organic phase and counted in a Beckman LS 6000IC scintillation counter to determine the radioactivity present in the lipids.

Subsequently 1 ml aliquots of the organic phase were evaporated to dryness under nitrogen, redissolved in 100 μl of chloroform:methanol (2:1 v/v), and transferred to a high performance thin layer chromotography plate (HPTLC, silica gel 60, 10×20 cm ex Merck). To resolve the various lipid classes, the plate was run successively with i) chloroform:methanol:acetone (76:20:4) to 15 and then 30 mm, ii) chloroform:methanol:acetone (79:12.5:8.5) to 80 mm, and finally iii) chloroform:ethyl acetate:diethyl ether:methanol (72:20:6:2) to 95 mm. After drying at 120 C. the plate was saturated with 15 ml of acidic copper sulphate solution (10% copper sulphate, 8% phosphoric acid) for 1 minute and then the lipids charred by heating to 120 C. for 1 minute and then 160 C. for 10 minutes. Lipid bands were identified using authentic lipid standards (Sigma Chemical Co.) and were quantified by reflectance densitometric scanning at 420 nm using a Shimadzu CS-9000 flying spot densitometer. Plates were then placed onto X-ray film (Amersham Multipurpose MP) in cassettes with intensifying screens and exposed for 1 to 4 weeks. Films were developed with a Fuji RGII X-ray film processor and bands quantified by transmission densitometric scanning at 530 nm using a Shimadzu CS-9000 flying spot densitometer.

Specific activity was calculated by dividing the radioactivity in each band by the mass of lipid in each band. Each lipid class was identified using authentic lipid standards.

2. Statistical Analysis

Mean values were compared using Students t test and significance was set at the 5% level.

3. Results

Figure 2:
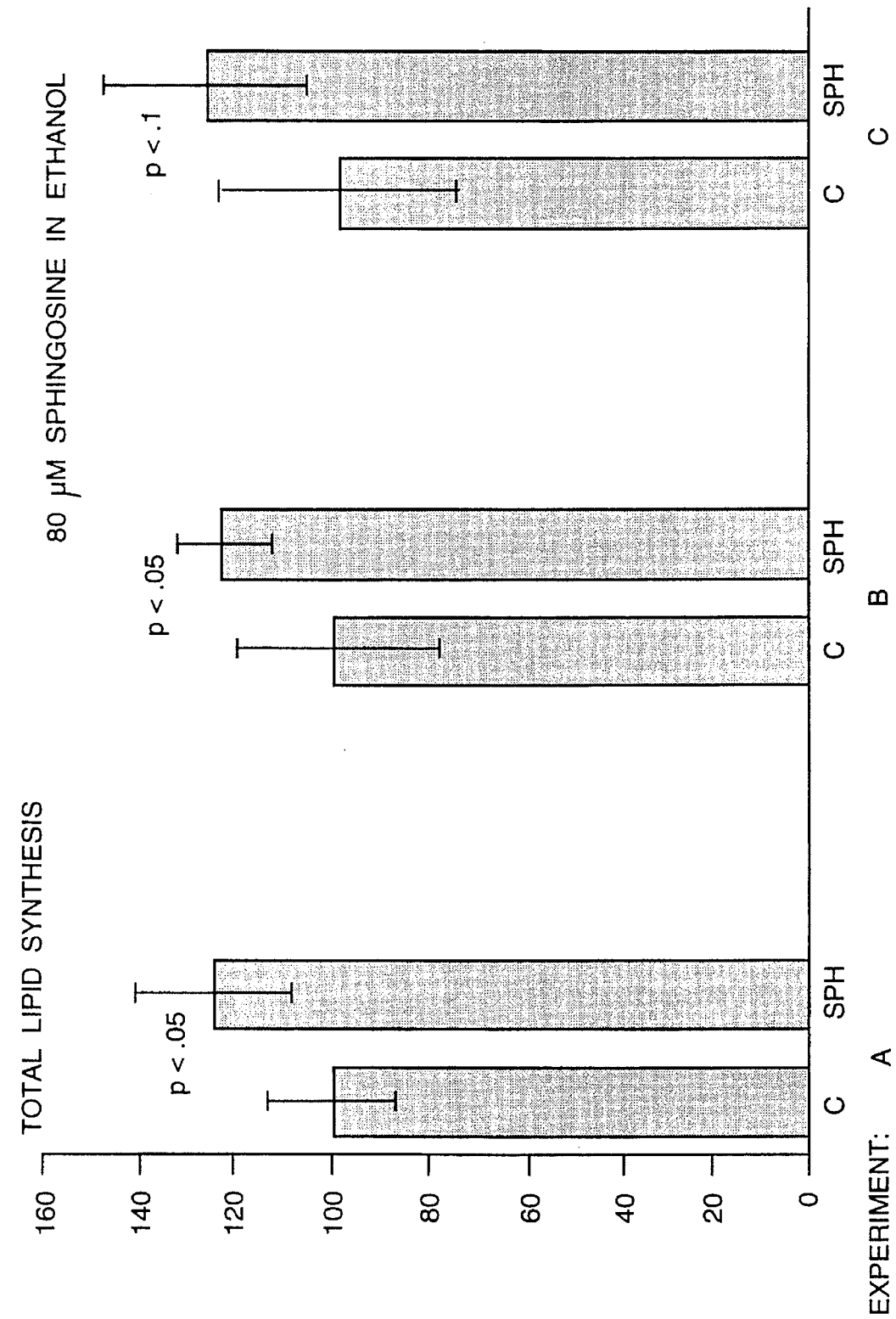
FIG. 2 illustrates the stimulatory effect of ceramide pathway intermediates on lipid levels in the epidermis on three separate occasions (experiments A–C).

The effect of the CPI, sphingosine, on epidermal lipid biosynthesis on three separate occasions: (Experiments A, B & C), is shown in FIG. 2. An increase in the level of radiolabelled acetate incorporated into epidermal lipids was evident when sphingosine (SPH) was present in the medium at a level of 0.08 mM, producing a consistent 20–25% increase over control (C, incubated without sphingosine) after 24 hours, indicating a reproducible stimulation of epidermal lipid biosynthesis.

The effect of sphingosine on individual lipid classes was determined using HPTLC. For each lipid class examined sphingosine at 0.08 mM increased the level of incorporation of radiolabelled acetate in comparison to the control (no sphingosine). The specific activity (radioactivity/lipid mass) for each lipid class and the ratio of sphingosine treated to control is shown in Table 1. The ceramide and glucosylceramide class showed the greatest increase in radioactivity incorporation following sphingosine treatment followed by non-polar lipids and finally phospholipids and cholesterol sulphate.

TABLE 2

Effect of sphingosine on the specific activity of various lipid classes

| Lipid | Specific Activity (radio activity/mass) | | Ratio SPH/C |
|---|---|---|---|
| | Control | Sphingosine | |
| Non-polar | 0.031 (0.017) | 0.066 (0.059) | 2.13 |
| Ceramide | 0.0085 (0.004) | 0.029 (0.028) | 3.40 |
| Glucosylceramide | 0.045 (0.024) | 0.136 (0.140) | 3.02 |
| Chol. sulphate | 0.297 (0.0762) | 0.424 (0.150) | 1.43 |
| Phospholipid | 0.264 (0.105) | 0.412 (0.193) | 1.56 |

Data shown as Mean (standard deviation), n=4 for control and sphingosine treated.

4. Conclusions

Sphingosine stimulates epidermal lipid biosynthesis, increasing the synthesis of all the lipid classes examined, but particularly the glucosylceramide and ceramide class.

Effect Ceramide Percursors on Keratinocyte Glucosylceramide Synthesis

1. Method

Human keratinocytes (ex clonetics were seeded in 6 well plates and allowed to reach 80% confluency after incubation in Keratinocyte Growth Medium (KGM ex clonetics, 0.15 mM calcium) at 37 C., 5% CO2. Fresh medium was added containing radiolabelled lipid precursor (2 µCi/ml of 1–14C acetic acid, sodium salt, 7.4 MBq/ml ex Amersham) and CPI (in 96% v/v ethanol vehicle) and incubated for 24 hours as above. Cells were harvested by scraping, lyophilized, and lipids extracted using 3 ml of chloroform:methanol solution (2:1 v/v) as above. Scintiverse BD scintillation fluid (10 ml ex Fisher) was added to 100 µl aliqouts of the organic phase and counted in a Beckman LS 6000 IC Scintillation counter to determine the radioactivity present in the lipids.

Subsequently, 200 µl aliqouts of the organic phase were applied to 1 cc aminopropyl-silica columns (ex Walters) and lipid fractions eluted by successive washes of hexane, chloroform:isopropanol (2:1 v/v), and acetic acid (2% v/v) in methanol. Radioactivity in each fraction was determined as above and compared to the total radioactivity of all the lipids. Furthermore fractions were evaporated to dryness, redissolved in 20 ul of chloroform:isopropanol (2:1 v/v) and lipid species present in each fraction identified by high performance thin layer chromatography as described in HPTLC for the organ culture experiments.

2. Statistical Analysis

Mean values were compared using students t test and significance was set at the 5% level.

3. Results

Figure 3:
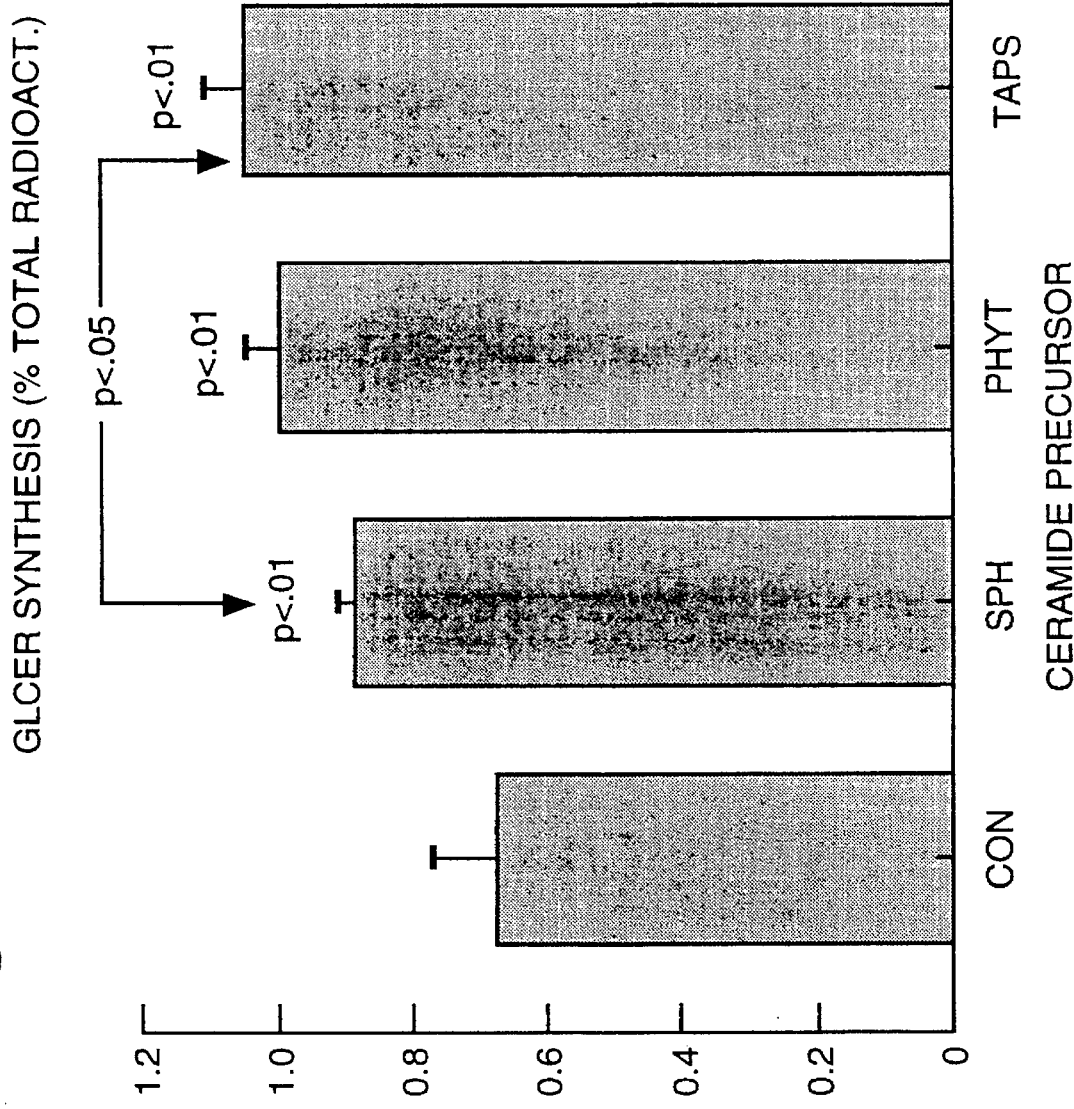
FIG. 3 illustrates the effects of ceramide pathway intermediates sphingozine, phytosphingozine and tetraacteylphytosphingozine on glucosylceramide synthesis.

The effects of the CPI's sphingosine (SPH), phytosphingosine (PHYT), and tetraacetylphytosphingosine (TAPS) on glucosylceramide synthesis (as identified by HPTLC) is shown in FIG. 3. A significant increase above control (no CPI present) over 24 hours in the proportion of radiolabelled acetate incorporated into all lipid was evident when CPI was present in the medium as a level of 0.02 mM, indicating a stimulation of keratinocyte glucosylceramide synthesis. Furthermore, TAPS produced a significantly higher proportion of radiolabel incorporated that SPH (FIG. 3) indicating that TAPS stimulates the synthesis of glucosylceramide more than SPH. PHYT was more effective that SPH, but less effective than TAPS.

Incorporation of Lipid Precursors into Ceramides/Cerebrosides in Keratinocytes in Culture Method
Cell Culture Human Keratinocytes were grown to 90% confluency in serum-free Keratinocyte Growth Medium (KGM, Clonetics Corporation, San Diego Calif.) containing 0.15 mM calcium. Cells were incubated with lipid precursors (phytosphingosine, tetraacetylphytosphingosine and juniperic acid) dissolved in ethanol for 24 h. Following incubation the cells were harvested in 1.8 mL of potassium chloride solution (0.88% w/v), the lipids extracted using chloroform:methanol, and the chloroform layer containing the lipids was anlysed by high performance thin layer chromatography.

Lipid Analysis:

The organic phase was dried under nitrogen, and resuspended in 200 µL of chloroform. Different lipid classes were separated based upon their polarity, using aminopropyl column chromatography. 200 µL of lipid was eluted with successive washes of hexane, hexane:ethyl acetate (85:15 v/v), and chloroform:isopropanol (2:1 v/v). The fractions were then evaporated to dryness under nitrogen, and resuspended in 100 µL of chloroform:methanol (2:1 v/v). ⅓ of the lipid was spotted onto high performance thin layer chromatography (HPTLC) silica gel plates and developed with an appropriate solvent system. Following lipid separation, the plate was dipped in a 10% copper sulphate solution, charred at 165° C. for 20 minutes, and quantified via reflectance densitometry.

Results

Tetra-acetyl phytosphingosine (TAPS) and phytosphingosine (PHYT) and juniperic acid (HA) were examined for their potential to generate phytoceramide 1, a ceramide 1-like molecule. Due to the extra hydroxyl group present on TAPS and PHYT compared with sphingosine the ceramide generated chromatographically migrates between ceramide 1 and 2. As can be seen from the results TAPS and HA produce significant amounts of phytoceramide 1. PHYT and HA, however, produce more of the glucosyl derivatives.

Conclusions

The combination of a sphingoid-base and an omega hydroxy fatty acid is capable of being used by keratinocytes to generate a ceramide 1-like molecule.

Effect of Ceramide I Precursors on Phytoceramide I Levels

| | | Phytoceramide I as % of total lipid | Standard Deviation |
|---|---|---|---|
| 1 | Control | 0.881 | 0.048 |
| 2 | HA | 0.816 | 0.125 |
| 3 | PHYT | 0.659 ** | 0.113 |
| 4 | HA + PHYT | 0.357 * | 0.070 |
| 5 | TAPS | 1.310 ** | 0.204 |
| 6 | HA + TAPS | 3.896 ** | 0.863 |

\* $P < 0.1$
\*\* $P < 0.5$

| | | Glucosylceramide I as % of total lipid | Standard Deviation |
|---|---|---|---|
| 1 | Control | 1.340 | 0.527 |
| 2 | HA | 1.526 | 0.284 |
| 3 | PHYT | 4.217 * | 1.000 |

| | Glucosylceramide I as % of total lipid | Standard Deviation |
|---|---|---|
| 4 HA + PHYT | 5.417 * | 0.900 |
| 5 TAPS | 4.424 * | 0.535 |
| 6 HA + TAPS | 1.577 | 0.493 |

* $P \leq 0.05$

Clinical Studies

1. Stratum Corneum Ceramide Levels Following Topical TAPS Treatment

In a one-month clinical study on 10 subjects, a 1% solution of tetraacetylphytosphinosine (TAPS) in an ethanol/propylene glycol (1:1) vehicle was applied to the volar forearm twice daily; an adjacent site on the forearm was treated with vehicle alone. The dosage amount was 100 μl applied to approximately 35 sq cm. After one month of treatment, a skin surface biopsy was taken from each site by tape-stripping with sellotape polyester tape. Each 'biopsy' consisted of eight consecutive tape strips of 2×3 cm each. Stratum corneum material was released from the tape by sonication in methanol, the methanol was dried off, and lipids were extracted in 2:1 chloroform:methanol. Solid phase extraction columns were used for preliminary lipid separation, followed by high performance thin layer chromatography (HPTLC) and densitometry for ceramide quantitation. The delipidized squames were incubated in protein extraction buffer, and protein content was determined by Pierce BCA assay.

| | ng Ceramide/μg Protein | | |
|---|---|---|---|
| Subject | Vehicle-treated | TAPS-treated | Change |
| 1 | 34.42 | 45.21 | + |
| 2 | 36.22 | 42.09 | + |
| 3 | 59.16 | 90.61 | + |
| 4 | 44.27 | 48.02 | + |
| 5 | 25.96 | 43.31 | + |
| 6 | 44.10 | 52.51 | + |
| 7 | 52.66 | 59.85 | + |
| 8 | 80.26 | 42.20 | − |
| 9 | 75.81 | 56.43 | − |
| 10 | 40.56 | 27.82 | − |
| Mean | 49.3 | 50.8 | |
| S.D. | 17.8 | 16.6 | |

Subjects showing increased ceramide levels following TAPS treatment (N=7):

| | nf Lipid/ug Protein | | |
|---|---|---|---|
| Treatment | Ceramide | Cholesterol | Fatty Acid |
| TAPS | 54.5 (17.1) | 24.2 (10.1) | 75.0 (49.1) |
| Vehicle | 42.4 (11.3) | 18.5 (4.4) | 55.7 (21.1) |
| Paired t-test | p = 0.015 | n.s.d. | n.s.d. |

Conclusions

These results show that TAPS improves the levels of ceramides in the stratum corneum but has no effect on cholesterol and fatty acid levels, indicating its specificity as a ceramide precursor.

EXAMPLES

The invention is illustrated by the following examples.

Example 1

This example illustrates a high internal phase water-in-oil emulsion.

A high internal phase water-in-oil emulsion having the following formulation was prepared:

| | % w/w |
|---|---|
| Fully hydrogenated coconut oil | 3.9 |
| phytoshingosine | 0.1 |
| Brij 92* | 5 |
| Bentone 38 | 0.5 |
| Preservative | 0.3 |
| $MgSO_4 7H_2O$ | 0.3 |
| Butylated hydroxy toluene | 0.01 |
| Perfume | qs |
| Water to | 100 |

*Brij 92 is polyoxyethylene (2) oleyl ether

Example 2

This example also illustrates a high internal phase water-in-oil emulsion in which the formulation of Example 1 was prepared but with the following changes:

i. liquid paraffin replaced the fully hydrogenated coconut oil, and ii. partially esterified phytosphingosine having the structure (11), replaced phytosphingosine per se.

Example 3

This example also illustrates a high internal phase water-in-oil emulsion in which the formulation of Example 1 was prepared, except that sphingosine replaced phytosphingosine per se.

Example 4

This example illustrates an oil-in-water cream.

An oil-in-water cream emulsion having the following formulation was prepared:

| | % w/w |
|---|---|
| Mineral oil | 4 |
| Sphingosine derivative having the structure (8) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water to | 100 |

*Brij 56 is cetyl alcohol POE (10)
Alfol 16RD is cetyl alcohol

Example 5

This example also illustrates an oil-in-water emulsion, in which the formulation of example 4 was prepared, except that the sphinganine derivative having the structure (5) replaced the sphingosine derivative having the structure (8).

Example 6

This example also illustrates an oil-in-water emulsion in which the formulation of example 4 was prepared, except that sphinganine replaced the sphingosine derivative having the structure (8).

Example 7

This example illustrates an alcoholic lotion according to the invention.

The lotion had the following formulation:

|  | % w/w |
|---|---|
| Phytosphingosine derivative having the structure (10) | 0.2 |
| Ethanol | 40 |
| Perfume | qs |
| Butylated hydroxy toluene | 0.01 |
| Water to | 100 |

Example 8

This example illustrates an alcoholic lotion containing a sphingosine derivative of the invention.

The lotion had the following formulations:

|  | % w/w |
|---|---|
| Sphingosine derivative having the structure (6) | 0.2 |
| Dimethylsulphoxide | 10 |
| Ethanol | 40 |
| Antioxidant | 0.1 |
| Perfume | qs |
| Water to | 100 |

Examples 9 and 10

The following compositions according to the invention represent lotions which can be used in the treatment of dry skin:

|  | % w/w | |
|---|---|---|
|  | 9 | 10 |
| phytosphingosine | 1.5 | — |
| Sphingosine having the structure (7) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water to | 100 | 100 |

Examples 11 and 12

The following compositions according to the invention represent lotions which can be used in the treatment of dry skin:

|  | % w/w | |
|---|---|---|
|  | 11 | 12 |
| sphiganine derivative having the structure (4) | 0.08 | — |
| sphinganine | — | 0.15 |
| Ethanol | 10 | 10 |
| Perfume | 0.5 | 0.5 |
| Distilled water to | 100 | 100 |

Example 13

This example illustrates a high internal phase water-in-oil emulsion.

A high internal phase water-in-oil emulsion having the following formulation was prepared:

|  | % w/w |
|---|---|
| Fully hydrogenated coconut oil | 3.9 |
| tetraacetyl phytoshingosine (Structure 2) | 0.1 |
| Brij 92* | 5 |
| Bentone 38 | 0.5 |
| Preservative | 0.3 |
| $MgSO_4 7H_2O$ | 0.3 |
| Butylated hydroxy toluene | 0.01 |
| Perfume | qs |
| Water to | 100 |

*Brij 92 is polyoxyethylene (2) oleyl ether

Example 14

This example illustrates an oil-in-water cream.

An oil-in-water cream emulsion having the following formulation was prepared:

|  | % w/w |
|---|---|
| Mineral oil | 4 |
| Sphingosine | 0.2 |
| Phytosphingosine | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water to | 10 |

*Brij 56 is cetyl alcohol POE (10)
Alfol 16RD is cetyl alcohol

Example 15

This example illustrates an alcoholic lotion.

The lotion had the following formulation:

|  | % w/w |
|---|---|
| Tetraacetyl phytosphingosine | 0.5 |
| Sphingosine | 0.2 |
| Ethanol | 40 |
| Perfume | qs |
| Butylated hydroxy toluene | 0.01 |
| Water to | 100 |

Example 16

This example illustrates an alcoholic lotion containing a sphinganine derivative of the invention.

The lotion had the following formulations:

|  | % w/w |
| --- | --- |
| Sphinganine derivative having the structure (3) | 0.2 |
| Dimethylsulphoxide | 10 |
| Ethanol | 40 |
| Antioxidant | 0.1 |
| Perfume | qs |
| Water to | 100 |

Examples 17 and 18

The following compositions according to the invention represent lotions which can be used in the treatment of dry skin:

|  | % w/w |
| --- | --- |
| N-acetyl phytosphingosine (Structure 9) | 1.5 |
| Perfume | 0.1 |
| Hydroxyethyl cellulose | 0.4 |
| Absolute ethanol | 25 |
| p-methyl benzoate | 0.2 |
| Sterilised demineralised water to | 100 |

We claim:

1. A composition suitable for topical application to human skin which comprises:

(i) from 0.0001% to 10% by weight of tetraacetyl phytosphingosine as a ceramide pathway intermediate; and (ii) a balancing amount of a cosmetically acceptable vehicle for the intermediate.

2. A composition according to claim 1, in which the ceramide pathway intermediate, tetracetyl buytosphingosine, from 0.01 to 5% by weight of the composition.

3. A composition according to claim 1 which further comprises a ceramide pathway adjunct selected from saturated or unsaturated alpha-, beta- or omega hydroxy fatty acids.

4. A composition according to claim 1, in which the adjunct is omega hydroxy linoleic acid, or an ester thereof.

5. A composition according to claim 1 which further comprises one or more ceramides.

6. A composition according to claim 1 which further comprises cholesterol.

7. A composition according to claim 1 which further comprises malonic acid.

8. A method of treating dry or damaged skin, which comprises the step of contacting the skin topically with one or more ceramide pathway intermediates or precursors thereof or mixtures thereof according to claim 1.

9. A method of treating skin to reduce or delay development of wrinkling associated with advancing age or with sun-induced skin ageing which comprises the step of contacting the skin topically with one or more ceramide pathway intermediates or precursors thereof or mixtures thereof according to claim 1.

* * * * *